(12) United States Patent
Furumiya et al.

(10) Patent No.: US 9,034,931 B2
(45) Date of Patent: May 19, 2015

(54) AQUEOUS OPHTHALMIC COMPOSITION

(75) Inventors: Chinatsu Furumiya, Osaka (JP); Takayuki Miyano, Osaka (JP); Atsuko Nakata, Osaka (JP); Eri Matsumoto, Osaka (JP)

(73) Assignee: ROHTO PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 13/995,893

(22) PCT Filed: Dec. 27, 2011

(86) PCT No.: PCT/JP2011/080163
§ 371 (c)(1),
(2), (4) Date: Jun. 19, 2013

(87) PCT Pub. No.: WO2012/090985
PCT Pub. Date: Jul. 5, 2012

(65) Prior Publication Data
US 2013/0296446 A1  Nov. 7, 2013

(30) Foreign Application Priority Data
Dec. 28, 2010  (JP) .................... 2010-292441

(51) Int. Cl.
*A61K 47/44* (2006.01)
*A61K 9/00* (2006.01)
*A61K 9/08* (2006.01)
*A61K 47/02* (2006.01)
*A61K 47/10* (2006.01)
*A61K 47/26* (2006.01)

(52) U.S. Cl.
CPC . *A61K 47/44* (2013.01); *A61K 9/08* (2013.01); *A61K 9/0048* (2013.01); *A61K 47/02* (2013.01); *A61K 47/10* (2013.01); *A61K 47/26* (2013.01)

(58) Field of Classification Search
CPC .................. A61K 47/44; A61K 9/0048
See application file for complete search history.

(56) References Cited

U.S. PATENT DOCUMENTS

| | | | |
|---|---|---|---|
| 6,228,049 B1 * | 5/2001 | Schroeder et al. ......... 604/93.01 |
| 2002/0010193 A1 | 1/2002 | Doi et al. |
| 2002/0052419 A1 | 5/2002 | Doi et al. |
| 2006/0100287 A1 | 5/2006 | Okajima et al. |
| 2007/0015693 A1 | 1/2007 | Chang et al. |
| 2009/0062381 A1 * | 3/2009 | Hirata et al. ................ 514/456 |
| 2010/0011989 A1 * | 1/2010 | Arita et al. ................. 106/217.8 |
| 2010/0239518 A1 * | 9/2010 | Matsumura et al. ....... 424/78.04 |
| 2013/0274332 A1 * | 10/2013 | Furumiya et al. ............ 514/547 |

FOREIGN PATENT DOCUMENTS

| | | |
|---|---|---|
| EP | 2 653 155 A1 | 9/2013 |
| EP | 2 730 292 A1 | 5/2014 |
| JP | 11-130667 | 5/1999 |
| JP | 11-180858 | 7/1999 |
| JP | 2002-003364 | 1/2002 |
| JP | 2002-356420 | 12/2002 |
| JP | 2004-315517 | 11/2004 |
| JP | 2006-151971 | 6/2006 |
| JP | 2006-321790 | 11/2006 |
| WO | 2007/075607 A1 | 7/2007 |
| WO | WO 2007075607 A1 * | 7/2007 |

OTHER PUBLICATIONS

International Search Report for PCT/JP2011/080163 dated Feb. 14, 2012.
Asada, H. et al. Suspension-type eye drop preparation, contains fluorometholone, and polyoxyethylene hydrogenated castor oil or polyoxyethylene castor oil. Database WPI, Section Ch, Week 200876, Thomson Scientific, London, GB, AN 2008-N01735, XP002733276, Nov. 6, 2008.

* cited by examiner

*Primary Examiner* — Sean Basquill
*Assistant Examiner* — Andrew S Rosenthal
(74) *Attorney, Agent, or Firm* — Roylance, Abrams, Berdo & Goodman, L.L.P.

(57) ABSTRACT

This invention relates to an aqueous ophthalmic composition comprising (A) polyoxyethylene castor oil in which the average number of moles of added ethylene oxide is 2 to 12 and (B) terpenoid. According to the present invention, an aqueous ophthalmic composition having an improved foam disappearance speed can be obtained.

8 Claims, No Drawings

AQUEOUS OPHTHALMIC COMPOSITION

TECHNICAL FIELD

The present invention relates to an aqueous ophthalmic composition.

BACKGROUND ART

In the field of ophthalmology, solubilizing agents are added to a variety of preparations. In particular, various solubilizing agents are added to aqueous ophthalmic compositions to help dissolution of biologically active components and additives with relatively low water solubility, and the like. One example of solubilizing agents used in the field of ophthalmology is a surfactant. An aqueous formulation containing a surfactant is known to foam easily, and foam is generated when subjected to vibration or impact during production or distribution.

In general, to use an aqueous ophthalmic composition in a manner safe on the eyes, the dissolution check during production is considered important. Of aqueous ophthalmic compositions, medical products such as eye drops and eye washes require foreign matter detection in the production steps. However, when foam is generated in the aqueous ophthalmic composition during production, and disappears at a low speed, the foam is difficult to distinguish from active ingredients and foreign matter. Consequently, dissolution check and foreign matter detection take a long period of time, preventing efficient production.

Terpenoid is sometimes added to an ophthalmic composition to provide a cooling sensation during application (see Patent Literature 1). Unfortunately, when an ophthalmic composition containing terpenoid is stored in a container, the terpenoid concentration is known to be reduced with time. This is presumably because of adsorption of terpenoid on the container, volatilization of terpenoid, or the like; however, an effective solution to this problem has not been found.

CITATION LIST

Patent Literature

PTL 1: JP2004-315517A

SUMMARY OF INVENTION

Technical Problem

The present invention was made in light of the prior art described above, and a main object is to provide an aqueous ophthalmic composition having a high foam disappearance speed when foam is generated by vibration or impact, particularly, the aqueous ophthalmic composition easily foaming due to inclusion of a solubilizing agent such as a surfactant.

Another object of the present invention is to provide a method for inhibiting reduction in terpenoid concentration over time in an aqueous ophthalmic composition containing terpenoid.

A further object of the present invention is to provide an aqueous ophthalmic composition having further improved various effects.

Solution to Problem

To solve the above problems, the present inventors conducted extensive research, and surprisingly found that the addition of both specific polyoxyethylene castor oil and terpenoid to an aqueous ophthalmic composition noticeably improves the foam disappearance speed when foam is generated by vibration or impact. According to further research, the present inventors found a problem such that an aqueous ophthalmic composition such as an eye drops in which a large amount of foam is generated has variation in the drip amount per use. Such a problem is particularly relevant in eye drops and solutions for wearing contact lenses used in a relatively small amount each time. Large variation in the drip amount causes disadvantages such as difficulty in controlling the amount per use by users and difficulty in handling. This may reduce compliance particularly when the aqueous ophthalmic composition is used as a medical product. The aqueous ophthalmic composition of the present invention, however, can reduce variation in the drip amount.

The present inventors also found that the addition of specific polyoxyethylene castor oil together with terpenoid attains the effect of inhibiting reduction in terpenoid concentration in an aqueous ophthalmic composition held in a container.

In further research, the present inventors found that an aqueous ophthalmic composition containing specific polyoxyethylene castor oil and terpenoid in combination enhances preservative efficacy. Typically, nonionic surfactants are known to have an effect of deactivating antiseptics, thereby reducing antiseptic action. For this reason, enhanced preservative efficacy attained by the combination use of terpenoid and specific polyoxyethylene castor oil, which is a nonionic surfactant, is a completely unexpected effect.

The present inventors also found the following as a result of extensive research. Polyoxyethylene castor oil in which the average number of moles of added ethylene oxide is 2 to 12 has low water solubility and is easily isolated in an aqueous solution; however, the addition of the polyoxyethylene castor oil together with terpenoid, which also has low water solubility, can surprisingly inhibit separation of the components in the aqueous ophthalmic composition, allowing for stable use for a long period of time. Specifically, in this research, the present inventors found that although the specific polyoxyethylene castor oil and terpenoid are each likely to precipitate or be isolated in an aqueous ophthalmic composition when used alone, the combination use of these components surprisingly provides an effect of inhibiting separation of both polyoxyethylene castor oil and terpenoid.

The present invention was accomplished as a result of further research based on these findings.

Specifically, the present invention provides ophthalmic compositions according to the following embodiments.

1-1. An aqueous ophthalmic composition comprising (A) polyoxyethylene castor oil in which the average number of moles of added ethylene oxide is 2 to 12 and (B) terpenoid.

1-2. The aqueous ophthalmic composition according to Item 1-1, wherein component (A) is at least one member selected from the group consisting of polyoxyethylene castor oil 3 and polyoxyethylene castor oil 10.

1-3. The aqueous ophthalmic composition according to Item 1-1 or 1-2, wherein the content of component (A) is 0.01 to 3 w/v % based on the total amount of the aqueous ophthalmic composition.

1-4. The aqueous ophthalmic composition according to any one of Items 1-1 to 1-3, wherein component (B) is at least one member selected from the group consisting of menthol, camphor, geraniol, borneol, and eucalyptus oil.

1-5. The aqueous ophthalmic composition according to any one of Items 1-1 to 1-4, wherein the content of component (B) is 0.0001 to 1 w/v % based on the total amount of the aqueous ophthalmic composition.

1-6. The aqueous ophthalmic composition according to any one of Items 1-1 to 1-5, wherein the total amount of component (B) is 0.01 to 1,000 parts by weight per 100 parts by weight of the total amount of component (A).

1-7. The aqueous ophthalmic composition according to any one of Items 1-1 to 1-6, wherein the total amount of component (B) is 2 to 15 parts by weight per 100 parts by weight of the total amount of component (A).

1-8. The aqueous ophthalmic composition according to any one of Items 1-1 to 1-7, which further comprises a buffer.

1-9. The aqueous ophthalmic composition according to any one of Items 1-1 to 1-8, wherein the buffer is a boric acid buffer.

1-10. The aqueous ophthalmic composition according to Item 1-8 or 1-9, wherein the content of the buffer is 0.01 to 10 w/v % based on the total amount of the aqueous ophthalmic composition.

1-11. The aqueous ophthalmic composition according to any one of Items 1-1 to 1-10, which further comprises a nonionic surfactant other than component (A).

1-12. The aqueous ophthalmic composition according to Item 1-11, wherein the nonionic surfactant other than component (A) is at least one member selected from the group consisting of polyoxyethylene sorbitan fatty acid esters, polyoxyethylene hydrogenated castor oils, polyoxyethylene-polyoxypropylene block copolymers, and polyoxyethylene castor oils in which the average number of moles of added ethylene oxide is 20 or more.

1-13. The aqueous ophthalmic composition according to Item 1-11 or 1-12, wherein the content of the nonionic surfactant other than component (A) is 0.001 to 3 w/v % based on the total amount of the aqueous ophthalmic composition.

1-14. The aqueous ophthalmic composition according to any one of Items 1-1 to 1-13, which is placed in a polyethylene terephthalate container.

1-15. The aqueous ophthalmic composition according to any one of Items 1-1 to 1-14, which is placed in a container on which a polyethylene nozzle is mounted.

1-16. The aqueous ophthalmic composition according to any one of Items 1-1 to 1-15, which is an eye drops.

1-17. The aqueous ophthalmic composition according to any one of Items 1-1 to 1-15, which is an eye wash.

1-18. The aqueous ophthalmic composition according to any one of Items 1-1 to 1-15, which is a solution for wearing a contact lens.

1-19. The aqueous ophthalmic composition according to any one of Items 1-1 to 1-15, which is a contact lens care solution.

The present invention provides methods for improving the foam disappearance speed in the aqueous ophthalmic composition, and methods for reducing variation in the drip amount during use according to the following embodiments.

2. A method for improving a foam disappearance speed in an aqueous ophthalmic composition, the method comprising adding (A) polyoxyethylene castor oil in which the average number of moles of added ethylene oxide is 2 to 12 and (B) terpenoid to the aqueous ophthalmic composition.

3. A method for improving a foam disappearance speed in an aqueous ophthalmic composition comprising (A) polyoxyethylene castor oil in which the average number of moles of added ethylene oxide is 2 to 12, the method comprising adding (B) terpenoid to the aqueous ophthalmic composition.

4. A method for reducing variation in drip amount during use in an aqueous ophthalmic composition, the method comprising adding (A) polyoxyethylene castor oil in which the average number of moles of added ethylene oxide is 2 to 12 and (B) terpenoid to the aqueous ophthalmic composition.

5. A method for improving a foam disappearance speed in an aqueous ophthalmic composition comprising a surfactant other than (A) polyoxyethylene castor oil in which the average number of moles of added ethylene oxide is 2 to 12, the method comprising adding component (A) and (B) terpenoid to the aqueous ophthalmic composition.

6. A method for reducing variation in drip amount during use in an aqueous ophthalmic composition comprising a surfactant other than (A) polyoxyethylene castor oil in which the average number of moles of added ethylene oxide is 2 to 12, the method comprising adding component (A) and (B) terpenoid to the aqueous ophthalmic composition.

The present invention provides methods for enhancing preservative efficacy in an aqueous ophthalmic composition according to the following embodiments.

7. A method for enhancing preservative efficacy in an aqueous ophthalmic composition, the method comprising adding (A) polyoxyethylene castor oil in which the average number of moles of added ethylene oxide is 2 to 12 and (B) terpenoid to the aqueous ophthalmic composition.

8. A method for enhancing preservative efficacy in an aqueous ophthalmic composition comprising (B) terpenoid, the method comprising adding (A) polyoxyethylene castor oil in which the average number of moles of added ethylene oxide is 2 to 12 to the aqueous ophthalmic composition.

The present invention also provides methods for inhibiting separation of an aqueous ophthalmic composition according to the following embodiments.

9. A method for inhibiting separation of an aqueous ophthalmic composition, the method comprising adding (A) polyoxyethylene castor oil in which the average number of moles of added ethylene oxide is 2 to 12 and (B) terpenoid to the aqueous ophthalmic composition.

10. A method for inhibiting separation of an aqueous ophthalmic composition comprising (A) polyoxyethylene castor oil in which the average number of moles of added ethylene oxide is 2 to 12, the method comprising adding (B) terpenoid to the aqueous ophthalmic composition.

11. A method for inhibiting separation of an aqueous ophthalmic composition comprising (B) terpenoid, the method comprising adding (A) polyoxyethylene castor oil in which the average number of moles of added ethylene oxide is 2 to 12 to the aqueous ophthalmic composition.

The present invention also provides methods for inhibiting reduction in terpenoid concentration over time according to the following embodiments.

12. A method for inhibiting reduction in terpenoid concentration over time in an aqueous ophthalmic composition held in a container, the method comprising adding (A) polyoxyethylene castor oil in which the average number of moles of added ethylene oxide is 2 to 12 and (B) terpenoid to the aqueous ophthalmic composition.

13. The method for inhibiting reduction in terpenoid concentration over time according to Item 12, wherein the container holding the aqueous ophthalmic composition is a polyethylene terephthalate container on which a polyethylene nozzle is mounted.

14. A method for imparting, to an aqueous ophthalmic composition containing (B) terpenoid and being held in a container, an effect of inhibiting reduction in terpenoid concentration over time in the aqueous ophthalmic composition, the method comprising adding (A) polyoxyethylene castor oil in which the average number of moles of added ethylene oxide is 2 to 12 to the aqueous ophthalmic composition.

15. The method according to Item 14, wherein the container holding the aqueous ophthalmic composition is a polyethylene terephthalate container on which a polyethylene nozzle is mounted.

The present invention also provides a method for maintaining cooling sensation of an aqueous ophthalmic composition according to the following embodiment.

16. A method for maintaining cooling sensation of an aqueous ophthalmic composition, the method comprising adding (A) polyoxyethylene castor oil in which the average number of moles of added ethylene oxide is 2 to 12 and (B) terpenoid to the aqueous ophthalmic composition.

The present invention also provides use according to the following embodiments.

17. Use of (A) polyoxyethylene castor oil in which the average number of moles of added ethylene oxide is 2 to 12 and (B) terpenoid, for production of an aqueous ophthalmic composition.

18. The use according to Item 17, wherein the aqueous ophthalmic composition is according to any one of Items 1-1 to 1-19.

Further, the present invention provides use according to the following embodiments.

19. Use of a composition as an aqueous ophthalmic composition, the composition comprising (A) polyoxyethylene castor oil in which the average number of moles of added ethylene oxide is 2 to 12 and (B) terpenoid.

20. The use according to Item 19, wherein the composition is according to any one of Items 1-1 to 1-19.

The present invention also provides compositions according to the following embodiments.

21. A composition for use as an aqueous ophthalmic composition, the composition comprising (A) polyoxyethylene castor oil in which the average number of moles of added ethylene oxide is 2 to 12 and (B) terpenoid.

22. The composition according to Item 21, which is recited in any one of Items 1-1 to 1-19.

The present invention further provides methods for producing an aqueous ophthalmic composition according to the following embodiments.

23. A method for producing an aqueous ophthalmic composition comprising adding (A) polyoxyethylene castor oil in which the average number of moles of added ethylene oxide is 2 to 12 and (B) terpenoid to a carrier containing water.

24. The method according to Item 23, wherein the aqueous ophthalmic composition is according to any one of Items 1-1 to 1-19.

Advantageous Effects of Invention

The present invention attains the following various effects.

(1) According to the present invention, the combination use of terpenoid and polyoxyethylene castor oil in which the average number of moles of added ethylene oxide is 2 to 12 can improve the foam disappearance speed in the aqueous ophthalmic composition. Consequently, dissolution check and foreign matter detection during the production of the aqueous ophthalmic composition can be performed in a short period of time, thus improving production efficacy.

(2) Since the aqueous ophthalmic composition of the present invention has the aforementioned feature, it reduces variation in the drip amount due to foaming during use. Therefore, the present invention enables easy control of the amount used and easy handling by users, thereby improving compliance.

(3) The aqueous ophthalmic composition of the present invention has enhanced preservative efficacy. Thus, even in the field of ophthalmology, which requires particularly high safety against bacterial contamination, it is possible to reduce contamination of the aqueous ophthalmic composition during use and the risk of microorganism infection or the like caused by the contamination.

(4) The aqueous ophthalmic composition of the present invention inhibits the reduction in terpenoid concentration over time when the composition is held in a container. This enables the composition to stably exhibit the cooling sensation due to terpenoid and the effect of the present invention for a long period of time.

(5) The aqueous ophthalmic composition of the present invention inhibits separation of poorly soluble components such as terpenoid and polyoxyethylene castor oil in which the average number of moles of added ethylene oxide is 2 to 12. This enables the composition to stably maintain the properties of the aqueous ophthalmic composition.

(6) The aqueous ophthalmic composition of the present invention can maintain a cooling sensation during use; therefore, the ophthalmic composition provides good feeling of use and can be used in a very comfortable manner.

The aqueous ophthalmic composition of the present invention has the aforementioned excellent effects and can be effectively used in a safer and more comfortable manner for a long period of time.

DESCRIPTION OF EMBODIMENTS

In the present specification, the unit of content "%" indicates w/v % and is the same as g/100 mL.

In the present specification, the abbreviation "POE" means polyoxyethylene unless otherwise specified.

In the present specification, the abbreviation "POP" means polyoxypropylene unless otherwise specified.

In the present specification, contact lenses include various types of contact lenses such as hard lenses, oxygen-permeable hard lenses, soft lenses (including silicone hydrogel lenses), and color lenses unless otherwise specified.

1. Aqueous Ophthalmic Composition

The aqueous ophthalmic composition of the present invention contains polyoxyethylene castor oil in which the average number of moles of added ethylene oxide is 2 to 12 (hereinafter sometimes referred to as component (A)). By using the polyoxyethylene castor oil in combination with terpenoid described below, the aforementioned excellent effects of the present invention can be attained.

Polyoxyethylene castor oil is a known compound obtained by addition polymerization of ethylene oxide with castor oil, and several kinds of polyoxyethylene castor oils having a different average number of moles of added ethylene oxide are known. The average number of moles of added ethylene oxide in the polyoxyethylene castor oil used as component (A) in the present invention is 2 to 12. Specific examples thereof include polyoxyethylene castor oil 3 in which the average number of moles of added ethylene oxide is 3, and polyoxyethylene castor oil 10 in which the average number of moles of added ethylene oxide is 10.

These polyoxyethylene castor oils may be used singly or in any combination of two or more. Note that polyoxyethylene castor oil used in the present invention is a compound that is different from and can be distinguished from polyoxyethylene hydrogenated castor oil obtained by addition polymerization of ethylene oxide with hydrogenated castor oil.

The content of component (A) in the aqueous ophthalmic composition of the present invention is suitably determined according to the kind of component (A), the kind of component (B) used in combination with component (A), the preparation form of the aqueous ophthalmic composition, etc. For example, the total amount of component (A) is 0.01 to 3 w/v %, preferably 0.02 to 2 w/v %, more preferably 0.02 to 1 w/v %, even more preferably 0.05 to 1 w/v %, even more preferably 0.05 to 0.6 w/v %, even more preferably 0.2 to 0.6 w/v %, particularly preferably 0.2 to 0.4 w/v %, and most preferably 0.2 to 0.3 w/v % based on the total amount of the aqueous ophthalmic composition of the present invention.

In the aqueous ophthalmic composition of the present invention, the amount of component (A) is preferably 0.05 to 0.3 w/v % to inhibit foaming of the aqueous ophthalmic composition, and the amount of component (A) is preferably 0.025 to 0.4 w/v % to attain the preservative efficacy of the aqueous ophthalmic composition.

The aforementioned content of component (A) is preferable to further improve an effect of improving the foam disappearance speed in the aqueous ophthalmic composition, effect of reducing variation in the drip amount during use, effect of improving preservative efficacy, or effect of inhibiting separation. The aforementioned content of component (A) is also preferable to further improve an effect of inhibiting the reduction in terpenoid concentration over time when the composition is contained in a container.

It is necessary for the ophthalmology composition of the present invention to contain terpenoid (hereinafter sometimes referred to as component (B)) in addition to component (A). The combination use of component (A) and component (B) attains the aforementioned effects, i.e., effects of improving the foam disappearance speed, reducing variation in the drip amount during use, inhibiting reduction in terpenoid concentration over time, enhancing preservative efficacy, inhibiting the separation of poorly soluble components, and the like.

Terpenoid used as component (B) is not particularly limited as long as it is pharmacologically (pharmaceutically) or physiologically acceptable in the field of medicine. Examples of the terpenoid include menthol, camphor, borneol, geraniol, cineol, citronellol, menthone, carvone, anethole, eugenol, limonene, linalool, linalyl acetate, and derivatives thereof. These compounds may be in the d form, l from, or dl form. Essential oil containing any of the above compounds can be used as terpenoid in the present invention. Examples of such essential oil include eucalyptus oil, bergamot oil, peppermint oil, cool mint oil, spearmint oil, mint oil, fennel oil, cinnamon oil, rose oil, and the like. These terpenoids can be used alone or in a combination of two or more.

Of components (B), menthol, camphor, geraniol, borneol, and the like are preferable to suitably exhibit the effects of the present invention. Examples of the preferable essential oil containing any of the above compounds include cool mint oil, peppermint oil, mint oil, camphor oil, eucalyptus oil, and the like. Menthol, camphor, geraniol, borneol, and eucalyptus oil are preferable examples, and l-menthol, d-camphor, dl-camphor, geraniol, d-borneol, and eucalyptus oil are further preferable examples.

To suitably exhibit the effects of the present invention, the content of component (B) in the aqueous ophthalmic composition of the present invention is 0.0001 to 1 w/v %, preferably 0.001 to 0.1 w/v %, more preferably 0.003 to 0.06 w/v %, and further preferably 0.003 to 0.02 w/v % based on the total amount of the aqueous ophthalmic composition of the present invention. When essential oil containing terpenoid is used as component (B), the content of the essential oil is determined such that the total amount of terpenoid in the essential oil is satisfied the aforementioned content.

The ratio of component (B) to component (A) in the aqueous ophthalmic composition of the present invention is not particularly limited as long as the aforementioned content is satisfied. To fully exhibit the effects of the present invention, i.e., improvement of the foam disappearance speed, inhibition of variation in the drip amount during use, inhibition of reduction in terpenoid concentration over time, enhancement of preservative efficacy, inhibition of separation of poorly soluble components, etc., it is desirable to satisfy the ratio such that the total amount of component (B) is 0.01 to 1,000 parts by weight, preferably 0.1 to 500 parts by weight, more preferably 0.5 to 100 parts by weight, even more preferably 0.5 to 80 parts by weight, particularly preferably 0.5 to 50 parts by weight, and most preferably 1 to 25 parts by weight relative to 100 parts by weight of the total amount of component (A). In particular, when the ratio is such that the total amount of component (B) is 2 to 15 parts by weight per 100 parts by weight of the total amount of component (A), the extremely excellent effects are exhibited.

As described below, various pharmacologically active components, biologically active components, etc., can be added, according to the purpose of use, to the aqueous ophthalmic composition of the present invention, and various kinds of additives can also be added. In this case, to improve the solubility of biologically active components, additives, etc., it is preferable to further add a surfactant other than component (A) as a solubilizing agent. Typically, the addition of such a surfactant increases foaming; however, even for an aqueous ophthalmic composition that is likely to make foam by the addition of a surfactant other than component (A), the foam disappearance speed can be increased by the addition of component (A) together with component (B) based on the aforementioned criteria. As a result, the production efficacy can be improved, and variation in the drip amount can be reduced. Furthermore, the effects of the present invention, such as inhibition of reduction in terpenoid concentration over time, can be further increased.

The surfactant other than component (A), which can be added to the aqueous ophthalmic composition of the present invention, is not particularly limited as long as it is a pharmacologically (pharmaceutically) or physiologically acceptable surfactant in the field of medicine. The surfactant may be a nonionic surfactant, ampholytic surfactant, anionic surfactant, or cationic surfactant.

Specific examples of the nonionic surfactant that can be added to the aqueous ophthalmic composition of the present invention include POE (20) sorbitan monolaurate (polysorbate 20), POE (20) sorbitan monopalmitate (polysorbate 40), POE (20) sorbitan monostearate (polysorbate 60), POE (20) sorbitan tristearate (polysorbate 65), POE (20) sorbitan monooleate (polysorbate 80), and like POE sorbitan fatty acid esters; POE (60) hydrogenated castor oil (polyoxyethylene hydrogenated castor oil 60) and like POE hydrogenated castor oils; POE (9) lauryl ether and like POE alkyl ethers; POE (20) POP (4) cetyl ether and like POE-POP alkyl ethers; POE (196) POP (67) glycol (poloxamer 407 and pluronic F127), POE (200) POP (70) glycol, and like polyoxyethylene-polyoxypropylene block copolymers; polyoxyethylene castor oil 20, polyoxyethylene castor oil 35, polyoxyethylene castor oil 40, polyoxyethylene castor oil 50, polyoxyethylene castor oil 60, and like polyoxyethylene castor oils in which the average number of moles of added ethylene oxide is 20 or more. In the compounds listed above, each of the numbers in the parentheses shows the number of moles of the added compounds.

Specific examples of the ampholytic surfactant that can be added to the aqueous ophthalmic composition of the present invention include alkyldiaminoethylglycine or salts thereof (e.g. hydrochloride).

Further, specific examples of the cationic surfactant that can be added to the aqueous ophthalmic composition of the present invention include benzalkonium chloride, benzethonium chloride, and the like.

Specific examples of the anionic surfactant that can be added to the aqueous ophthalmic composition of the present invention include alkylbenzene sulfonate, alkyl sulfate, polyoxyethylene alkyl sulfate, aliphatic α-sulfomethyl ester, α-olefin sulfonic acid, and the like.

Nonionic surfactants are preferable, and POE sorbitan fatty acid esters, POE hydrogenated castor oils, POE-POP block copolymers, and polyoxyethylene castor oils in which the average number of moles of added ethylene oxide is 20 or more are more preferable. Polysorbate 80, polyoxyethylene hydrogenated castor oil 60, poloxamer 407, and polyoxyethylene castor oil 35 are particularly preferable.

In the aqueous ophthalmic composition of the present invention, the surfactants other than component (A) can be used singly or in a combination of two or more.

When the surfactant is added to the aqueous ophthalmic composition of the present invention, the content of the surfactant is suitably determined according to the kind of the surfactant, the kinds and the contents of other components, the preparation form of the aqueous ophthalmic composition, etc. For example, the total amount of the surfactant other than component (A) is 0.001 to 3 w/v %, preferably 0.01 to 2 w/v %, more preferably 0.05 to 1 w/v %, and particularly preferably 0.1 to 1 w/v % based on the total amount of the aqueous ophthalmic composition.

The aqueous ophthalmic composition of the present invention preferably includes a buffer, by which the pH of the aqueous ophthalmic composition of the present invention can be adjusted. A buffer that can be added to the aqueous ophthalmic composition of the present invention is not particularly limited as long as it is a pharmacologically (pharmaceutically) or physiologically acceptable buffer in the field of medicine. Examples of such a buffer include boric acid buffers, phosphoric acid buffers, carbonic acid buffers, citric acid buffers, acetic acid buffers, aspartic acid, aspartic acid salts, and the like. These buffers can be used in combination. Examples of boric acid buffers include boric acid or boric acid salts such as alkali metal salt of boric acid and alkaline earth metal salt of boric acid. Examples of phosphoric acid buffers include phosphoric acid or phosphoric acid salts such as alkali metal phosphate and alkaline earth metal phosphate. Examples of carbonic acid buffers include carbonic acid or carbonic acid salts such as alkali metal carbonate and alkaline earth metal carbonate. Examples of citric acid buffers include citric acid or alkali metal citrate, alkaline earth metal citrate, and the like. As a boric acid buffer or a phosphoric acid buffer, a hydrate of boric acid salt or a hydrate of phosphoric acid salt can be used. More specifically, examples of the boric acid buffer include boric acid or salts thereof (sodium borate, potassium tetraborate, potassium metaborate, ammonium borate, borax, etc.); examples of the phosphoric acid buffer include phosphoric acid or salts thereof (disodium hydrogen phosphate, sodium dihydrogen phosphate, potassium dihydrogen phosphate, trisodium phosphate, dipotassium phosphate, calcium monohydrogen phosphate, calcium dihydrogen phosphate, etc.); examples of the carbonic acid buffer include carbonic acid or salts thereof (sodium bicarbonate, sodium carbonate, ammonium carbonate, potassium carbonate, calcium carbonate, potassium bicarbonate, magnesium carbonate, etc.); examples of the citric acid buffer include citric acid or salts thereof (sodium citrate, potassium citrate, calcium citrate, sodium dihydrogen citrate, disodium citrate, etc.); examples of the acetic acid buffer include acetic acid or salts thereof (ammonium acetate, potassium acetate, calcium acetate, sodium acetate, etc.), and aspartic acid or salts thereof (sodium aspartate, magnesium aspartate, potassium aspartate, etc.). Of the buffers, boric acid buffers (especially, combination of boric acid and borax) are preferable.

When the buffer is added to the aqueous ophthalmic composition of the present invention, the content of the buffer cannot be uniformly determined, and it varies depending on the kind of the buffer to be used, the kinds and contents of the other components, the preparation form of the aqueous ophthalmic composition, etc. For example, the total amount of the buffer is 0.01 to 10 w/v %, preferably 0.05 to 5 w/v %, more preferably 0.1 to 2.5 w/v %, and even more preferably 0.1 to 1 w/v % based on the total amount of the aqueous ophthalmic composition.

The aqueous ophthalmic composition of the present invention may further include a tonicity agent. The tonicity agent that can be added to the aqueous ophthalmic composition of the present invention is not particularly limited as long as it is a pharmacologically (pharmaceutically) or physiologically acceptable tonicity agent in the field of medicine. Examples of the tonicity agent include disodium hydrogen phosphate, sodium dihydrogen phosphate, potassium dihydrogen phosphate, sodium hydrogen sulfite, sodium sulfite, potassium chloride, calcium chloride, sodium chloride, magnesium chloride, potassium acetate, sodium acetate, sodium bicarbonate, sodium carbonate, sodium tiosulfate, magnesium sulfate, glycerin, propylene glycol, and the like. Of these tonicity agents, preferable examples include glycerin, propylene glycol, sodium chloride, potassium chloride, calcium chloride, and magnesium chloride. Sodium chloride and glycerin are more preferable, and sodium chloride is particularly preferable. These tonicity agents can be used singly or in a combination of two or more.

When a tonicity agent is added to the aqueous ophthalmic composition of the present invention, the content of the tonicity agent cannot be uniformly determined, and it varies depending on the kind of the tonicity agent to be used. For example, the total amount of the tonicity agent is 0.01 to 10 w/v %, preferably 0.05 to 5 w/v %, and more preferably 0.1 to 3 w/v %, based on the total amount of the aqueous ophthalmic composition.

The pH of the aqueous ophthalmic composition of the present invention is not particularly limited as long as it is within a pharmacologically (pharmaceutically) or physiologically acceptable range in the field of medicine. The pH of the aqueous ophthalmic composition of the present invention is, for example, 4.0 to 9.5, preferably 5.0 to 9.0, more preferably 6.2 to 8.5, even more preferably 6.5 to 8, and particularly preferably about 6.5 to 7.5.

The osmotic pressure of the aqueous ophthalmic composition of the present invention is not particularly limited as long as it is within a range acceptable to the human body. The osmotic pressure ratio of the aqueous ophthalmic composition of the present invention is, for example, preferably 0.5 to 5.0, more preferably 0.6 to 3.0, and particularly preferably 0.7 to 2.0. The osmotic pressure can be adjusted using an inorganic salt, polyhydric alcohol, sugar alcohol, sugar, etc., according to a known method in the technical field of the present invention. The osmotic pressure ratio is the ratio of the osmotic pressure of a sample to 286 mOsm (osmotic pressure of 0.9 w/v % aqueous sodium chloride solution) based on the Japanese Pharmacopoeia, $15^{th}$ revision. The osmotic pressure can be measured with reference to the osmotic measurement method (freezing point depression method) described in the Japanese Pharmacopoeia. To obtain a reference solution (0.9 w/v % sodium chloride solution) for measuring the osmotic pressure ratio, sodium chloride (standard reagent according to the Japanese Pharmacopoeia) is dried for 40 to 50 minutes at 500 to 650° C., and then allowed to cool in a desiccator (silica gel). 0.900 g of the resultant is accurately measured, and the resultant is then dissolved in purified water, thus accurately preparing 100 mL of the solution. Alternatively, a commercially available reference solution (0.9 w/v % aqueous sodium chloride solution) for measuring the osmotic pressure ratio can be used.

As long as the effects of the present invention are attained, the aqueous ophthalmic composition of the present invention may include, in addition to the aforementioned components, a suitable amount of a various pharmacologically active component and/or a biologically active component singly or in combination. Such components are not particularly limited, and examples include effective components in ophthalmological drugs described in, for example, Standards for Approval for the Manufacture (Import) of Non-prescription Drugs 2000 (*Ippanyou Iyakuhin Seizou (yunyuu) syounin Kizyun* 2000), compiled under supervision of the Pharmaceutical Council. Specific examples of the components used in ophthalmological drugs include the following components.

Antihistamines such as iproheptine, diphenhydramine hydrochloride, chlorphenylamine maleate, ketotifen fumarate, and pemirolast potassium.

Decongestants such as tetrahydrozoline hydrochloride, naphazoline hydrochloride, naphazoline sulfate, epinephrine hydrochloride, ephedrine hydrochloride, and methylephedrine hydrochloride.

Disinfectants such as cetyl pyridinium, benzalkonium chloride, benzethonium chloride, chlorhexidine hydrochloride, chlorhexidine gluconate, and polyhexanide hydrochloride.

Vitamins such as flavin adenine dinucleotide sodium, cyanocobalamin, retinol acetate, retinol palmitate, pyridoxine hydrochloride, pantenol, calcium pantothenate, and tocopherol acetate.

Amino acids such as potassium aspartate and magnesium aspartate.

Antiphlogistics such as dipotassium glycyrrhizinate, pranoprofen, allantoin, azulene, sodium azulene sulfonate, guaiazulene, berberine chloride, berberine sulfate, lysozyme chloride, and licorice.

Others such as sodium cromoglicate, sodium chondroitin sulfate, sodium hyaluronate, sulfamethoxazole, and sodium sulfamethoxazole.

Further, as long as the effects of the invention are attained, various additives can be suitably selected and added to the aqueous ophthalmic composition by a known method according to the application, preparation form, etc. The additives can be added singly or in a combination in a suitable amount. Examples of the additives include those described in Japanese Pharmaceutical Excipients Directory 2007 (edited by the International Pharmaceutical Excipients Council Japan). Typical components include the following additives.

Carriers such as water, water-containing ethanol, and like aqueous carriers.

Sugars such as cyclodextrin.

Sugar alcohols such as xylitol, sorbitol, and mannitol, wherein these compounds may be in the d form, l form, or dl form.

Antiseptics, disinfectants, and antibacterial agents such as alkyldiaminoethylglycine hydrochloride, sodium benzoate, ethanol, benzalkonium chloride, benzetonium chloride, chlorhexidine gluconate, chloro butanol, sorbic acid, potassium sorbate, sodium dehydroacetate, methyl parahydroxybenzoate, ethyl parahydroxybenzoate, propyl parahydroxyben- zoate, butyl parahydroxybenzoate, oxyquinoline sulfate, phenethyl alcohol, benzyl alcohol, and Glokill (trade name, Rhodia Co., Ltd.).

The aqueous ophthalmic composition of the present invention can be prepared by adding a desired amount of each of component (A) and component (B), and if necessary, other components to a carrier in a manner such that the aqueous ophthalmic composition has a desired concentration. For example, eye drops, solutions for wearing contact lenses, eye washes, or contact lens care solutions are prepared by dissolving or suspending the aforementioned components in purified water, adjusting the pH and osmotic pressure to the predetermined levels, and subjecting these to sterilization treatment by filter sterilization, etc. Regarding the dissolution of components (A) and (B), and the dissolution of components with a high hydrophobic property, components having an effect of helping dissolution such as surfactants may be added beforehand, then the mixture is stirred, after which purified water is added thereto, followed by dissolution or suspension.

The present invention provides, as a method for producing an aqueous ophthalmic composition, a method comprising adding (A) polyoxyethylene castor oil in which the average number of moles of added ethylene oxide is 2 to 12 and (B) terpenoid to a water-containing carrier.

The aqueous ophthalmic composition of the present invention means an ophthalmic composition in which the content of water exceeds 85 w/v % or more based on the total amount of the aqueous ophthalmic composition. The content of water in the aqueous ophthalmic composition is preferably 90 w/v % or more, more preferably 92 w/v % or more, even more preferably 95 w/v % or more, and particularly preferably 97 w/v % or more. Pharmacologically (pharmaceutically), or physiologically acceptable water in the field of medicine can be used as the water used in the aqueous ophthalmic composition of the present invention. Examples of water include distilled water, water, purified water, sterile purified water, water for injection, distilled water for injection, and the like. The dosage form of the aqueous ophthalmic composition in the present invention is not particularly limited as long as it is usable in the field of ophthalmology. The dosage form is preferably liquid. These definitions are based on the Japanese Pharmacopoeia, $15^{th}$ revision.

Examples of the aqueous ophthalmic composition of the present invention include eye drops (also called as ophthalmic solutions or ophthalmic drugs) [note that examples of the eye drops also include eye drops that can be instilled into the eyes during use of contact lenses], eye washes (also referred to as collyria or eye lotions) [note that examples of the eye washes also include eye washes that can wash the eyes during use of contact lenses], solutions for wearing contact lenses, contact lens care products, (disinfectant solutions for contact lenses, storage solutions for contact lenses, cleansing solutions for contact lenses, cleansing-storage solutions for contact lenses, and disinfectant-storage-cleansing solutions for contact lenses (multiple-purpose solutions for contact lenses)), etc. The aqueous ophthalmic composition of the present invention ensures an improved foam disappearance speed and low variation in the drip amount during use. Thus, in particular, the aqueous ophthalmic composition of the present invention is preferably used in eye drops and solutions for wearing contact lenses, which are used in a particularly small amount each time, and is particularly preferably used in eye drops.

The aqueous ophthalmic composition of the present invention has an excellent antiseptic effect due to improved preservative efficacy, and it has an excellent effect of inhibiting the reduction in terpenoid concentration over time. For this reason, the present invention is preferably used as a multi-dose aqueous ophthalmic composition, i.e., an aqueous ophthalmic composition that is used more than once after the commercial product is opened. The aqueous ophthalmic composition can be stably stored for a few days, a few weeks, or longer.

As the container that holds the aqueous ophthalmic composition of the present invention, a container that can be typically used to hold an aqueous ophthalmic composition can be used. The container may be made of glass or plastic. When a plastic container is used to hold the aqueous ophthalmic composition of the present invention, although constituent materials of the plastic container are not particularly limited, polyethylenenaphthalate, polyarylate, polyethylene terephthalate, polypropylene, polyethylene, and polyimide can be used alone or in a mixture of two or more, or as a copolymer thereof. Examples of the copolymers include copolymers that contain other polyester units or imide units, in addition to any one of ethylene-2,6-naphthalate units, arylate units, ethylene terephthalate units, propylene units, ethylene units, and imide units, which is contained as a main component. In the present invention, for example, a polyethylene terephthalate container means a container in which polyethylene terephthalate is contained in an amount of 50 w/w % or more based on the total weight of the constituent materials of the container.

Of these containers, although a polyethylene terephthalate container is excellent in view of durability and cost, reduction in terpenoid concentration over time can be sometimes observed when the composition is contained in a polyethylene terephthalate container. Even when the aqueous ophthalmic composition of the present invention is held in a polyethylene terephthalate container, the combination use of specific polyoxyethylene castor oil and terpenoid inhibits reduction in terpenoid concentration over time; thus, the polyethylene terephthalate container can be effectively used. In particular, even in a container having polyethylene terephthalate of 75 w/w % or more, and particularly 95 w/w % or more based on the total weight of the constituent materials of the container, the container can be effectively used without noticeably reducing the concentration of terpenoid over time.

The structure, constituent materials, etc., of a container spout periphery such as a nozzle mounted on a container containing the aqueous ophthalmic composition of the present invention are not particularly limited. The structure of the container spout periphery such as a nozzle may be a typically applicable structure as a spout (e.g., nozzle) of a container for ophthalmologic compositions (e.g., container for eye drops), and the nozzle may be integrally or separately formed with the container. Examples of the constituent materials of the spout periphery or spout (e.g., nozzle) include those mentioned in the constituent materials of the plastic containers.

In particular, to attain further improved flexibility, reasonable cost, and/or an effect of reducing variation in the drip amount, a spout containing polyethylene or polypropylene as a constituent material is preferable. However, such materials used for a nozzle are likely to cause reduction in terpenoid concentration over time. This is presumably because terpenoid is likely to adsorb to these materials. The aqueous ophthalmic composition of the present invention can inhibit reduction in terpenoid concentration over time by the combination use of specific polyoxyethylene castor oil and terpenoid, even when the composition is contained in a container having a spout that contains polyethylene or polypropylene as a constituent material. Thus, a container having a spout that contains polyethylene or polypropylene as a constituent material can be effectively used.

Examples of polyethylene include high-density polyethylene, low-density polyethylene, and the like. Of these, a spout containing low-density polyethylene as a constituent material is preferable. As a spout, a nozzle used in a container for eye drops is preferable.

As a preferable combination of a container that holds the aqueous ophthalmic composition of the present invention and a container spout periphery, it is possible to use a combination of a polyethylene terephthalate container and a polyethylene container spout periphery, more preferably a combination of a polyethylene terephthalate eye drop container and a polyethylene nozzle, and particularly preferably, a combination of a polyethylene terephthalate eye drop container and a low-density polyethylene nozzle. Such a combination can significantly exhibit the effect of reducing variation in the drip amount in the present invention.

The aqueous ophthalmic composition of the present invention has an effect of inhibiting reduction in terpenoid concentration over time. Thus, even when a container including a container body and a container spout periphery made of the materials mentioned above is used, the cooling sensation due to terpenoid can be stably maintained for a long period of time, and the composition of the present invention can stably exhibit an effect attained by the combination use of specific polyoxythylene castor oil and terpenoid for a long period of time.

Since the aqueous ophthalmic composition of the present invention can increase the foam disappearance speed, reduce variation in the drip amount during use, and can be instilled into an eye in a constant amount per use, it is particularly preferably used as eye drops containing a pharmacologically active component and/or a biologically active component. Such eye drops can be used as eye drops for relieving itchy eyes, eye drops for relieving eye strain, and the like.

From a different viewpoint, the present invention also provides use of (A) polyoxyethylene castor oil in which the average number of moles of added ethylene oxide is 2 to 12 and (B) terpenoid, for production of an aqueous ophthalmic composition.

From another different viewpoint, the present invention also provides use of a composition as an aqueous ophthalmic composition, the composition comprising (A) polyoxyethylene castor oil in which the average number of moles of added ethylene oxide is 2 to 12 and (B) terpenoid From still another different viewpoint, the present invention provides a composition for use as an aqueous ophthalmic composition, the composition comprising (A) polyoxyethylene castor oil in which the average number of moles of added ethylene oxide is 2 to 12 and (B) terpenoid.

2. Method for Improving Foam Disappearance Speed and Method for Reducing Variation in Drip Amount As mentioned above, in the aqueous ophthalmic composition of the present invention, by using component (A) and component (B) in combination, the foam disappearance speed can be improved in the aqueous ophthalmic composition and variation in the drip amount during use can be reduced.

Therefore, from a different viewpoint, the present invention provides a method for improving the foam disappearance speed in an aqueous ophthalmic composition, the method comprising adding (A) polyoxyethylene castor oil in which the average number of moles of added ethylene oxide is 2 to 12 and (B) terpenoid to the aqueous ophthalmic composition.

The present invention also provides a method for improving the foam disappearance speed in an aqueous ophthalmic composition comprising (A) polyoxyethylene castor oil in which the average number of moles of added ethylene oxide is 2 to 12, the method comprising adding (B) terpenoid to the aqueous ophthalmic composition.

The present invention further provides a method for reducing variation in the drip amount during use of an aqueous ophthalmic composition, the method comprising adding (A) polyoxyethylene castor oil in which the average number of moles of added ethylene oxide is 2 to 12 mol and (B) terpenoid to the aqueous ophthalmic composition.

The present invention still further provides a method for improving the foam disappearance speed in an aqueous ophthalmic composition comprising a surfactant other than component (A), and a method for reducing variation in the drip amount during use of the aqueous ophthalmic composition, each method comprising adding (A) polyoxyethylene castor oil in which the average number of moles of added ethylene oxide is 2 to 12 and (B) terpenoid to the aqueous ophthalmic composition.

In these methods, the kinds of component (A) and component (B) to be used, the contents (or amounts added) and the ratio thereof, the kinds and the contents (amounts added) of components added other than the above, the preparation form of the aqueous ophthalmic composition, the kind and the combination of the container, the embodiment manner, and the like, are the same as in the "1. Aqueous Ophthalmic Composition" section above.

In particular, the methods described above are suitably used when the aqueous ophthalmic composition is used as an eye drops or a solution for wearing a contact lens.

3. Method for Enhancing Preservative Efficacy

As described above, the preservative efficacy in the aqueous ophthalmic composition can be enhanced by using component (A) and component (B) in combination.

Accordingly, from another viewpoint, the present invention provides a method for enhancing preservative efficacy in an aqueous ophthalmic composition, the method comprising adding (A) polyoxyethylene castor oil in which the average number of moles of added ethylene oxide is 2 to 12 and (B) terpenoid to the aqueous ophthalmic composition.

The present invention also provides a method for enhancing preservative efficacy in an aqueous ophthalmic composition comprising terpenoid (B), the method comprising adding (A) polyoxyethylene castor oil in which the average number of moles of added ethylene oxide is 2 to 12 to the aqueous ophthalmic composition.

In these methods, the kinds of components (A) and (B) to be used, the contents (amounts added) and the ratio thereof, the kinds and the contents (amounts added) of components added other than the above, the preparation form of the aqueous ophthalmic composition, the kind and the combination of the container, the embodiment manner, and the like, are the same as in the "1. Aqueous Ophthalmic Composition" section above.

In particular, these methods are preferably used when the aqueous ophthalmic composition is a multi-dose aqueous ophthalmic composition, i.e., an aqueous ophthalmic composition used more than one time after the commercial product is opened. Examples of such an aqueous ophthalmic composition include multi-dose eye drops, multi-dose eye washes, multi-dose solutions for wearing contact lenses, and multi-dose contact lens care products.

4. Method for Inhibiting Separation

As described above, the combination use of component (A) and component (B) can inhibit separation of poorly soluble components such as components (A) and (B) from the aqueous ophthalmic composition, and can stabilize the properties of the preparation.

Thus, from a different viewpoint, the present invention provides a method for inhibiting separation of an aqueous ophthalmic composition, the method comprising adding (A) polyoxyethylene castor oil in which the average number of moles of added ethylene oxide is 2 to 12 and (B) terpenoid to the aqueous ophthalmic composition. The present invention also provides a method for inhibiting separation of an aqueous ophthalmic composition comprising (A) polyoxyethylene castor oil in which the average number of moles of ethylene oxide is 2 to 12, the method comprising adding (B) terpenoid to the aqueous ophthalmic composition. The present invention further provides a method for inhibiting separation of an aqueous ophthalmic composition comprising (B) terpenoid, the method comprising adding (A) polyoxyethylene castor oil in which the average number of moles of added ethylene oxide is 2 to 12 to the aqueous ophthalmic composition.

In the aforementioned methods, the kinds, the contents (amounts added), and the ratio of components (A) and (B), the kinds and the contents (amounts added) of components added other than the above, and the preparation form of the aqueous ophthalmic composition, the kind and the combination of the container, the embodiment manner, and the like are the same as in the "1. Aqueous Ophthalmic Composition" section above.

5. Method for Inhibiting Reduction in Terpenoid Concentration Over Time

As described above, the combination use of components (A) and (B) can inhibit the reduction of the concentration of component (B) over time when the aqueous ophthalmic composition containing these components is held in a container. This is presumably because the combination use of components (A) and (B) can inhibit the adsorption of component (B) in the aqueous ophthalmic composition to the container, volatilization of component (B) from the container, and the like. Thus, it is possible to maintain the cooling sensation of the aqueous ophthalmic composition and the effect of the present invention over a long period of time.

Therefore, from a different viewpoint, the present invention provides a method for inhibiting reduction in terpenoid concentration over time in an aqueous ophthalmic composition held in a container, the method comprising adding (A) polyoxyethylene castor oil in which the average number of moles of added ethylene oxide is 2 to 12 and (B) terpenoid to the aqueous ophthalmic composition.

The present invention further provides the above-described method for inhibiting reduction in terpenoid concentration over time, wherein the container holding the aqueous ophthalmic composition is a polyethylene terephthalate container on which a polyethylene nozzle is mounted.

From another different viewpoint, the present invention provides a method for imparting, to an aqueous ophthalmic composition containing (B) terpenoid and being held in a container, an effect of inhibiting reduction in terpenoid concentration over time in the aqueous ophthalmic composition, the method comprising adding (A) polyoxyethylene castor oil in which the average number of moles of added ethylene oxide is 2 to 12 to the aqueous ophthalmic composition.

The present invention also provides the above-described method for imparting an effect of inhibiting reduction in terpenoid concentration over time to the aqueous ophthalmic composition, wherein the container holding the aqueous ophthalmic composition is a polyethylene terephthalate container on which a polyethylene nozzle is mounted.

In these methods, the kinds, the contents (amounts added), and the ratio of components (A) and (B) to be used, the kinds and the contents (amounts added) of components added other than the above, the preparation form of the aqueous ophthalmic composition, the kind and the combination of the container, the embodiment manner, etc., are the same as those in the "1. Aqueous Ophthalmic Composition" section above.

In particular, these methods are preferably used in eye drops and solutions for wearing contact lenses.

6. Method for Maintaining Cooling Sensation

As described above, the combination use of components (A) and (B) in the aqueous ophthalmic composition can maintain the cooling sensation of the aqueous ophthalmic composition. Thus, the cooling sensation of the aqueous ophthalmic composition when the composition is instilled into the eyes can be maintained.

Therefore, from a different viewpoint, the present invention provides a method for maintaining the cooling sensation of an aqueous ophthalmic composition, the method comprising adding (A) polyoxyethylene castor oil in which the average number of moles of added ethylene oxide is 2 to 12 and (B) terpenoid to the aqueous ophthalmic composition.

In these methods, the kinds, the contents (amounts added), and the ratio of components (A) and (B) to be used, the kinds and the contents (amounts added) of components added other than the above, the preparation form of the aqueous ophthalmic composition, the kind and the combination of the container, the embodiment manner, etc., are the same as those in the "1. Aqueous Ophthalmic Composition" section above.

In particular, these methods are preferably used in eye drops and solutions for wearing contact lenses.

EXAMPLES

The present invention is described below in more detail with reference to Test Examples and Examples. However, the scope of the invention is not limited to these Examples.

Test Example 1

Foam Disappearance Speed Test (1)

Aqueous ophthalmic compositions having the formulations shown in the following Table 1 (Example 1-1 and Comparative Example 1-1) were prepared by a standard method, and foam disappearance speeds were evaluated using these compositions. Specifically, foaming upon shaking and foam disappearance speeds after the elapse of a certain period of time were evaluated in the aqueous ophthalmic composition containing a surfactant and the aqueous ophthalmic composition containing a terpenoid in addition to such a surfactant.

First, each of the aqueous ophthalmic compositions shown in Table 1 (Comparative Example 1-1 and Example 1-1) was prepared. This test used l-menthol that conforms to the standard of the Japanese Pharmacopoeia, 15th revision, and polyoxyethylene castor oil 10 that conforms to the standard for polyoxyethylene castor oil in Japanese Pharmaceutical Excipients 2003 and in which the average number of moles of added ethylene oxide is 10.

Subsequently, each of the aqueous ophthalmic compositions in an amount of 30 mL was placed in individual 50-mL glass centrifuge tubes, and the tubes were shaken 1,500 times using a Recipad Shaker SR-2w (TAITEC). Immediately after shaking, a foam part and an aqueous solution part were confirmed by visual observation, and the volume of the foam part was measured. The tubes were then allowed to stand, the volume of the foam part was measured over time, and foam disappearance speeds were evaluated by measuring the time required for the foam to completely disappear. The results are also shown in Table 1.

TABLE 1

| | Unit (w/v %) | |
|---|---|---|
| | Comparative Example 1-1 | Example 1-1 |
| Polyoxyethylene castor oil 10 | 0.3 | 0.3 |
| l-menthol | — | 0.03 |
| Boric acid | 0.5 | 0.5 |
| Borax | 0.02 | 0.02 |
| Glycerin | 2.5 | 2.5 |
| Purified water (mL) | Balance | Balance |
| pH | 7 | 7 |
| Time required for the foam to completely disappear (minutes) | 165 | 15 |

The volume of the foam part of Example 1-1 measured immediately after shaking was similar to that of Comparative Example 1-1. However, after 1 minute, the volume of the foam part of Example 1-1 was decreased to about one-eighth of that of Comparative Example 1-1. Further, as shown in Table 1, the time required for the foam to completely disappear was 165 minutes in the aqueous ophthalmic composition containing polyoxyethylene castor oil 10 but not containing a terpenoid (menthol) (Comparative Example 1-1), whereas the foam completely disappeared in only 15 minutes in the aqueous ophthalmic composition containing both polyoxyethylene castor oil 10 and a terpenoid (menthol) (Example 1-1).

Test Example 2

Foam Disappearance Speed Test (2)

As shown in the following Table 2, aqueous ophthalmic compositions containing a surfactant other than component (A) (polysorbate 80) (Example 1-2 and Comparative Examples 1-2 to 1-4) were prepared by a standard method. This test used l-menthol and polysorbate 80 that conform to the standard of the Japanese Pharmacopoeia, 15th revision, and polyoxyethylene castor oil 10 and polyoxyethylene castor oil 35 that conform to the standard for polyoxyethylene castor oil in Japanese Pharmaceutical Excipients 2003 and in which the average number of moles of added ethylene oxide is 10 and 35, respectively.

Using these aqueous ophthalmic compositions, a foam disappearance speed test was performed in the same manner as in Test Example 1. Foam disappearance speeds were evaluated by measuring the time required for the initial foam to be reduced by half. The results are also shown in Table 2.

TABLE 2

| | Unit (w/v %) | | | |
|---|---|---|---|---|
| | Comparative Example 1-2 | Comparative Example 1-3 | Comparative Example 1-4 | Example 1-2 |
| l-menthol | — | 0.03 | 0.03 | 0.03 |
| Polyoxyethylene castor oil 10 | 0.3 | — | — | 0.3 |

TABLE 2-continued

| | Comparative Example 1-2 | Comparative Example 1-3 | Comparative Example 1-4 | Example 1-2 |
|---|---|---|---|---|
| | Unit (w/v %) | | | |
| Polyoxyethylene castor oil 35 | — | — | 0.3 | — |
| Polysorbate 80 | 0.3 | 0.3 | 0.3 | 0.3 |
| Boric acid | 0.5 | 0.5 | 0.5 | 0.5 |
| Borax | 0.02 | 0.02 | 0.02 | 0.02 |
| Purified water (mL) | Balance | Balance | Balance | Balance |
| pH | 7 | 7 | 7 | 7 |
| Time required for the foam to be reduced by half (minutes) | 120 | 450 | 380 | 50 |

Regarding volumes of the foam part measured immediately after shaking in Example 1-2 and Comparative Examples 1-2 to 1-4, the volumes of the foam part of Comparative Examples 1-3 and 1-4 and Example 1-2 were similar, although the volume of the foam part of Comparative Example 1-2 was about 30% larger than the volumes of the foam part of the other three preparations. As shown in Table 2, however, the time required for the foam to be reduced by half was 120 minutes in the aqueous ophthalmic composition containing polyoxyethylene castor oil 10 and polysorbate 80 (Comparative Example 1-2), and 450 minutes in the aqueous ophthalmic composition containing menthol and polysorbate 80 (Comparative Example 1-3).

In contrast, the foam was reduced by half in only 50 minutes in the aqueous ophthalmic composition containing polyoxyethylene castor oil 10, menthol, and polysorbate 80 (Example 1-2). In the aqueous ophthalmic composition containing polyoxyethylene castor oil 35 instead of polyoxyethylene castor oil 10 (Comparative Example 1-4), it took 380 minutes.

The above results reveal that the combined use of polyoxyethylene castor oil 10 and a terpenoid also significantly improves the speed at which foam generated in the presence of another surfactant (e.g., polysorbate 80) disappears. This effect was very small when polyoxyethylene castor oil 35 was used instead of polyoxyethylene castor oil 10.

Test Example 3

Foam Disappearance Speed Test (3)

As shown in the following Tables 3 to 5, aqueous ophthalmic compositions containing a surfactant other than component (A) (polysorbate 80) (Examples 1-3 to 1-12 and Comparative Examples 1-5 and 1-6) were prepared by a standard method. This test used l-menthol, eucalyptus oil, and polysorbate 80 that conform to the standard of the Japanese Pharmacopoeia, 15th revision, and geraniol that conforms to the standard of Japanese Pharmaceutical Excipients 2003. This test also used polyoxyethylene castor oil 3 that conforms to the standard for polyoxyethylene castor oil in Japanese Pharmaceutical Excipients 2003 and in which the average number of moles of added ethylene oxide is 3.

Using these aqueous ophthalmic compositions, a foam disappearance speed test was performed in the same manner as in Test Example 1. Foam disappearance speeds were evaluated by measuring the time required for the initial foam to be reduced by half. The results are also shown in Tables 3 to 5.

TABLE 3

| | Comparative Example 1-5 | Example 1-3 | Example 1-4 | Example 1-5 |
|---|---|---|---|---|
| | Unit (w/v %) | | | |
| Polyoxyethylene castor oil 3 | 0.05 | 0.05 | 0.05 | 0.05 |
| l-menthol | — | 0.005 | — | — |
| Geraniol | — | — | 0.005 | — |
| Eucalyptus oil | — | — | — | 0.005 |
| Polysorbate 80 | 0.05 | 0.05 | 0.05 | 0.05 |
| Boric acid | 0.5 | 0.5 | 0.5 | 0.5 |
| Borax | 0.02 | 0.02 | 0.02 | 0.02 |
| Purified water (mL) | Balance | Balance | Balance | Balance |
| pH | 7 | 7 | 7 | 7 |
| Time required for the foam to be reduced by half (minutes) | 120 | 30 | 60 | 70 |

TABLE 4

| | Example 1-6 | Example 1-7 | Example 1-8 | Example 1-9 | Example 1-10 |
|---|---|---|---|---|---|
| | Unit (w/v %) | | | | |
| Polyoxyethylene castor oil 3 | 0.05 | 0.05 | 0.05 | 0.05 | 0.05 |
| l-menthol | 0.005 | 0.005 | 0.015 | — | — |
| Geraniol | 0.005 | — | — | 0.03 | — |
| Eucalyptus oil | — | 0.05 | — | — | 0.03 |
| Polysorbate 80 | 0.05 | 0.05 | 0.05 | 0.05 | 0.05 |
| Boric acid | 0.5 | 0.5 | 0.5 | 0.5 | 0.5 |
| Borax | 0.02 | 0.02 | 0.02 | 0.02 | 0.02 |
| Purified water (mL) | Balance | Balance | Balance | Balance | Balance |
| pH | 7 | 7 | 7 | 7 | 7 |
| Time required for the foam to be reduced by half (minutes) | 60 | 60 | 70 | 100 | 90 |

TABLE 5

| | Comparative Example 1-6 | Example 1-11 | Example 1-12 |
|---|---|---|---|
| | Unit (w/v %) | | |
| Polyoxyethylene castor oil 10 | 0.05 | 0.05 | 0.05 |
| l-menthol | — | 0.005 | — |
| Geraniol | — | — | 0.005 |
| Polysorbate 80 | 0.05 | 0.05 | 0.05 |
| Boric acid | 0.5 | 0.5 | 0.5 |
| Borax | 0.02 | 0.02 | 0.02 |
| Purified water (mL) | Balance | Balance | Balance |
| pH | 7 | 7 | 7 |
| Time required for the foam to be reduced by half (minutes) | 70 | 30 | 30 |

As is clear from Tables 3 and 4, the time required for the foam to be reduced by half was significantly shortened in the aqueous ophthalmic compositions containing polyoxyethylene castor oil 3 and containing l-menthol, geraniol, or eucalyptus oil, compared to the aqueous ophthalmic composition containing only polyoxyethylene castor oil 3 (Comparative Example 1-5 and Examples 1-3 to 1-10).

Similarly, as is clear from Table 5, the time required for the foam to be reduced by half was significantly shortened in the aqueous ophthalmic compositions containing polyoxyethylene castor oil 10 and containing l-menthol or geraniol, compared to the aqueous ophthalmic composition containing only polyoxyethylene castor oil 10 (Comparative Example 1-6 and Examples 1-11 and 1-12).

Test Example 4

Foam Disappearance Speed Test (4)

As shown in the following Table 6, aqueous ophthalmic compositions containing a surfactant other than component (A) (polyoxyethylene castor oil 35) (Examples 1-13 and 1-14 and Comparative Examples 1-7 and 1-8) were prepared by a standard method. In the preparation of the aqueous ophthalmic compositions, borax was added in an amount such that the pH of each aqueous ophthalmic composition was 7. This test used d-camphor that conforms to the standard of the Japanese Pharmacopoeia, 15th revision, and d-borneol that conforms to the standard of Japanese Pharmaceutical Excipients 2003. This test also used polyoxyethylene castor oil 3, polyoxyethylene castor oil 10, and polyoxyethylene castor oil 35 that conform to the standard for polyoxyethylene castor oil in Japanese Pharmaceutical Excipients 2003 and in which the average number of moles of added ethylene oxide is 3, 10, and 35, respectively.

Using these aqueous ophthalmic compositions, a foam disappearance speed test was performed in the same manner as in Test Example 1 except that the amount of the composition placed was 20 mL. Foam disappearance speeds were evaluated by measuring the time required for the initial foam to be reduced by half. The results are also shown in Table 6.

TABLE 6

| | Comparative Example 1-7 | Comparative Example 1-8 | Example 1-13 | Example 1-14 |
|---|---|---|---|---|
| | Unit (w/v %) | | | |
| Polyoxyethylene castor oil 3 | 0.25 | — | 0.25 | — |
| Polyoxyethylene castor oil 10 | — | 0.25 | — | 0.25 |
| Polyoxyethylene castor oil 35 | 0.25 | 0.25 | 0.25 | 0.25 |
| d-camphor | — | — | 0.005 | — |
| d-borneol | — | — | — | 0.005 |
| Boric acid | 0.2 | 0.2 | 0.2 | 0.2 |
| Borax | q.s. | q.s. | q.s. | q.s. |
| Purified water | Balance | Balance | Balance | Balance |
| pH | 7 | 7 | 7 | 7 |
| Time required for the foam to be reduced by half (minutes) | 300 | 390 | 160 | 100 |

As shown in Table 6, the time required for the foam to be reduced by half was 300 minutes in the formulation containing polyoxyethylene castor oil 3 and polyoxyethylene castor oil 35 (Comparative Example 1-7), and 390 minutes in the aqueous ophthalmic composition containing polyoxyethylene castor oil 10 and polyoxyethylene castor oil 35 (Comparative Example 1-8).

On the other hand, the foam was reduced by half in only 160 minutes in the aqueous ophthalmic composition containing polyoxyethylene castor oil 3, polyoxyethylene castor oil 35, and camphor (Example 1-13), and in only 100 minutes in the aqueous ophthalmic composition containing polyoxyethylene castor oil 10, polyoxyethylene castor oil 35, and borneol (Example 1-14).

Test Example 5

Foam Disappearance Speed Test (5)

As shown in the following Table 7, aqueous ophthalmic compositions containing a surfactant other than component (A) (polysorbate 80) (Examples 1-15 to 1-17 and Comparative Examples 1-9 and 1-10) were prepared by a standard method. This test used l-menthol and polysorbate 80 that conform to the standard of the Japanese Pharmacopoeia, 15th revision, and polyoxyethylene castor oil 3 and polyoxyethylene castor oil 10 that conform to the standard for polyoxyethylene castor oil in Japanese Pharmaceutical Excipients 2003 and in which the average number of moles of added ethylene oxide is 3 and 10, respectively.

Using these aqueous ophthalmic compositions, a foam disappearance speed test was performed in the same manner as in Test Example 1. Foam disappearance speeds were evaluated by measuring the time required for the initial foam to be reduced by half. The results are also shown in Table 7.

TABLE 7

| | Comparative Example 1-9 | Example 1-15 | Comparative Example 1-10 | Example 1-16 | Example 1-17 |
|---|---|---|---|---|---|
| Unit (w/v %) | | | | | |
| Polyoxyethylene castor oil 3 | 0.05 | 0.05 | — | — | — |
| Polyoxyethylene castor oil 10 | — | — | 0.2 | 0.2 | 0.2 |
| l-menthol | — | 0.1 | — | 0.01 | 0.1 |
| Polysorbate 80 | 0.5 | 0.5 | 0.5 | 0.5 | 0.5 |
| Boric acid | 0.5 | 0.5 | 0.5 | 0.5 | 0.5 |
| Borax | 0.02 | 0.02 | 0.02 | 0.02 | 0.02 |
| Purified water (mL) | Balance | Balance | Balance | Balance | Balance |
| pH | 7 | 7 | 7 | 7 | 7 |
| Time required for the foam to be reduced by half (minutes) | 80 | 25 | 430 | 100 | 25 |

As is clear from Table 7, the time required for the foam to be reduced by half was significantly shortened in the aqueous ophthalmic compositions containing l-menthol together with polyoxyethylene castor oil 3 or polyoxyethylene castor oil 10, compared to the aqueous ophthalmic compositions containing only polyoxyethylene castor oil 3 or polyoxyethylene castor oil 10 (Comparative Examples 1-9 and 1-10, and Examples 1-15 to 1-17).

Test Example 6

Foam Disappearance Speed Test (6)

As shown in the following Table 8, aqueous ophthalmic compositions containing both polyoxyethylene castor oil 3 and polyoxyethylene castor oil 10 as component (A) and containing a surfactant other than component (A) (polysorbate 80) (Examples 1-18 and 1-19) were prepared by a standard method. This test used l-menthol and polysorbate 80 that conform to the standard of the Japanese Pharmacopoeia, 15th revision, and polyoxyethylene castor oil 3 and polyoxyethylene castor oil 10 that conform to the standard for polyoxyethylene castor oil in Japanese Pharmaceutical Excipients 2003 and in which the average number of moles of added ethylene oxide is 3 and 10, respectively.

Using these aqueous ophthalmic compositions, a foam disappearance speed test was performed in the same manner as in Test Example 1. Foam disappearance speeds were evaluated by measuring the time required for the initial foam to be reduced by half. The results are shown in the following Table 8.

TABLE 8

| | Example 1-18 | Example 1-19 |
|---|---|---|
| Unit (w/v %) | | |
| Polyoxyethylene castor oil 3 | 0.1 | 0.05 |
| Polyoxyethylene castor oil 10 | 0.1 | 0.1 |
| l-menthol | 0.02 | 0.01 |
| Polysorbate 80 | 0.2 | 0.2 |
| Boric acid | 0.5 | 0.5 |
| Borax | 0.02 | 0.02 |
| Purified water (mL) | Balance | Balance |

TABLE 8-continued

| | Example 1-18 | Example 1-19 |
|---|---|---|
| Unit (w/v %) | | |
| pH | 7 | 7 |
| Time required for the foam to be reduced by half (minutes) | 25 | 50 |

As shown in Table 8, it was found that the use of l-menthol together with both polyoxyethylene castor oil 3 and polyoxyethylene castor oil 10 significantly shortened the time required for the foam to be reduced by half.

The above results reveal that when a terpenoid is contained, the speed at which generated foam disappears is significantly improved also in aqueous ophthalmic compositions wherein polyoxyethylene castor oils in which the average number of moles of added ethylene oxide is 2 to 12 are used in combination.

Test Example 7

Test on Foam Disappearance Speeds and Drip Amounts

Aqueous ophthalmic compositions shown in the following Table 9 (Examples 2-1 to 2-3 and Comparative Examples 2-1 and 2-2) were prepared by a standard method, and foam disappearance speeds and drip amounts were evaluated. This test used l-menthol and polysorbate 80 that conform to the standard of the Japanese Pharmacopoeia, 15th revision, and geraniol and polyoxyethylene hydrogenated castor oil 60 that conform to the standard of Japanese Pharmaceutical Excipients 2003. This test also used polyoxyethylene castor oil 10 that conforms to the standard for polyoxyethylene castor oil in Japanese Pharmaceutical Excipients 2003 and in which the average number of moles of added ethylene oxide is 10.

First, each of the aqueous ophthalmic compositions in an amount of 6.5 mL was placed in individual 13-mL eye drop containers made of polyethylene terephthalate, and each container was equipped with a nozzle made of low-density polyethylene to prepare eye drops. Separately, a sheet of filter paper was placed in a measurement container, the measurement container was sealed with a lid, and the total weight (initial value) of the sheet of filter paper and the measurement container was measured. While the nozzle of each eye drop container was held horizontal (container turned sideways), one drip of the aqueous ophthalmic composition was placed in the measurement container. The measurement container was subsequently sealed with the lid. The total weight of the sheet of filter paper into which the aqueous ophthalmic composition was absorbed and the measurement container was measured, and the amount (weight) of one drip was determined by subtracting the initial value from the measured total weight. This was repeated 10 times, and variation that occurred among the drips was further calculated as an SD value (SD value of the drip amount before shaking).

After the eye drop containers were vigorously shaken up and down 20 times, they were allowed to stand for 10 minutes. Thereafter, the amount (weight) of one drip was measured in the same manner as described above, and variation that occurred among the 10 drips was calculated as an SD value (SD value of the drip amount after shaking).

The rate of change in the SD values before and after shaking was determined as the rate of change in variation by the following formula. The results are also shown in Table 9.

Rate of change in variation(times)=$SD$ value after shaking/$SD$ value before shaking

TABLE 9

Unit (w/v %)

| | Comparative Example 2-1 | Comparative Example 2-2 | Example 2-1 | Example 2-2 | Example 2-3 |
|---|---|---|---|---|---|
| Polyoxyethylene castor oil 10 | 0.3 | 0.5 | 0.3 | 0.5 | 0.5 |
| l-menthol | — | — | 0.03 | 0.03 | — |
| Geraniol | — | — | — | — | 0.01 |
| Polysorbate 80 | 0.3 | — | 0.3 | — | — |
| Polyoxyethylene hydrogenated castor oil 60 | — | 0.5 | — | 0.5 | 0.5 |
| Boric acid | 0.5 | 0.5 | 0.5 | 0.5 | 0.5 |
| Borax | 0.02 | 0.02 | 0.02 | 0.02 | 0.02 |
| Purified water (mL) | Balance | Balance | Balance | Balance | Balance |
| pH | 7 | 7 | 7 | 7 | 7 |
| Rate of change in variation (times) | 2.1 times | 2.7 times | 1.3 times | 1.1 times | 1.7 times |

The SD value of the drip amount after shaking was about twice that before shaking in Comparative Example 2-1, whereas the SD value of the drip amount after shaking was only about 1.3 times that before shaking in Example 2-1. Specifically, it was found that compared to Comparative Example 2-1, the rate of change in variation was significantly smaller in Example 2-1, indicating that variation in the drip amount was inhibited even after shaking. A similar tendency was also observed from comparison of Comparative Example 2-2 with Example 2-2 and Example 2-3.

The above results reveal that according to the aqueous ophthalmic composition of the present invention, which contains both polyoxyethylene castor oil 10 and a terpenoid, the drip amount during use is stabilized even when such a composition foams during distribution, due to carrying by the user or other causes.

Test Example 8

Separation Inhibition Test

Aqueous ophthalmic compositions shown in the following Table 10 (Example 3-1 and Comparative Example 3-1) were prepared by a standard method, and the presence of separation was evaluated by visual observation. This test used l-menthol that conforms to the standard of the Japanese Pharmacopoeia, 15th revision, and polyoxyethylene castor oil 10 that conforms to the standard for polyoxyethylene castor oil in Japanese Pharmaceutical Excipients 2003 and in which the average number of moles of added ethylene oxide is 10. Specifically, the state of the aqueous ophthalmic compositions was confirmed by visual observation immediately after preparation. Subsequently, 1 mL of each aqueous ophthalmic composition was placed in individual Eppendorf tubes and centrifuged at 6000 G for 3 minutes using a centrifuge (MX-100 TOMY) to separate materials of different specific gravities, and the state of the aqueous ophthalmic compositions was confirmed again by visual observation after centrifugation. The results are also shown in Table 10.

TABLE 10

Unit (w/v %)

| | Comparative Example 3-1 | Example 3-1 |
|---|---|---|
| Polyoxyethylene castor oil 10 | 0.3 | 0.3 |
| l-menthol | — | 0.03 |
| Boric acid | 0.5 | 0.5 |
| Borax | 0.02 | 0.02 |
| Propylene glycol | 1 | 1 |
| Purified water | Balance | Balance |
| Total amount | 100 mL | 100 mL |
| Visual observation before centrifugation | Not separated | Not separated |
| Visual observation after centrifugation | Separated | Not separated |

Both the aqueous ophthalmic compositions were uniformly cloudy liquid when the state of the aqueous ophthalmic compositions was confirmed by visual observation immediately after preparation (before centrifugation). From the visual observation of the state of the aqueous ophthalmic compositions after centrifugation, however, it was confirmed that the aqueous ophthalmic composition of Comparative Example 3-1 had been separated into a transparent aqueous solution part and a white solid that was assumed to be polyoxyethylene castor oil 10. On the other hand, the aqueous ophthalmic composition of Example 3-1 was uniformly cloudy liquid both before and after centrifugation, with no precipitate observed. From this fact, it was confirmed that separation was inhibited and each component was uniformly present in the aqueous ophthalmic composition of Example 3-1.

The above results reveal that despite its relatively low water solubility, polyoxyethylene castor oil 10 is surprisingly less likely to separate in aqueous ophthalmic compositions when used in combination with l-menthol, which also has low water solubility.

Test Example 9

Particle Size Measurement Test

Aqueous ophthalmic compositions shown in the following Table 11 (Example 3-2 and Comparative Example 3-2) were prepared by a standard method, and particle size in each of the aqueous ophthalmic compositions was measured using a particle size measurement device (FPAR-1000 (Otsuka Electronics Co., Ltd.)). This test used l-menthol that conforms to the standard of the Japanese Pharmacopoeia, 15th revision, and polyoxyethylene hydrogenated castor oil 60 that conforms to the standard of Japanese Pharmaceutical Excipients 2003. This test also used polyoxyethylene castor oil 10 that conforms to the standard for polyoxyethylene castor oil in Japanese Pharmaceutical Excipients 2003 and in which the average number of moles of added ethylene oxide is 10. The results are also shown in Table 11.

Detailed measurement conditions are as follows.

| Measurement conditions | |
|---|---|
| Temperature | 25° C. |
| ND value | Auto (10% or 25%) |
| Probe | for concentrated solutions |
| Measurement time | 180 seconds |
| Number of repetition | 1 |
| Dust cutting | 10 times (upper: 10%, lower: 1,000%) |
| Light Amount Adjustment | |
| Homodyne light amount optimum value | 30,000 cps |
| Max | 50,000 cps |
| Min | 10,000 cps |
| Analysis technique | |
| Marquardt (lambda: 1,000, iteration: 1,000) | |

TABLE 11

| | Unit (w/v %) | |
|---|---|---|
| | Comparative Example 3-2 | Example 3-2 |
| Polyoxyethylene castor oil 10 | 0.15 | 0.15 |
| l-menthol | — | 0.02 |
| Polyoxyethylene hydrogenated castor oil 60 | 0.15 | 0.15 |
| Boric acid | 0.5 | 0.5 |
| Borax | 0.05 | 0.05 |
| Purified water | Balance | Balance |
| Total amount | 100 mL | 100 mL |

The average particle size of Comparative Example 3-2 was about 1.4 times the average particle size of Example 3-2. This test was performed to measure the particle sizes of micelles in the aqueous ophthalmic compositions in which solubility had been improved by adding a nonionic surfactant (polyoxyethylene hydrogenated castor oil 60) in addition to polyoxyethylene castor oil 10. Since it is presumed that micelles with smaller particle sizes are less likely to coalesce, and thus separation tends not to occur, it can be said that separation is less likely to occur in Example 3-2 than in Comparative Example 3-2.

Test Example 10

Test on Reduction in Terpenoid Concentration over Time

Aqueous ophthalmic compositions shown in the following Table 12 (Example 4-1 and Comparative Examples 4-1 and 4-2) were prepared by a standard method. Each of the aqueous ophthalmic compositions was placed in individual eye drop containers made of polyethylene terephthalate (hereinafter referred to as PET) and a test was performed to confirm the change in the concentration of menthol. This test used l-menthol that conforms to the standard of the Japanese Pharmacopoeia, 15th revision, and polyoxyethylene hydrogenated castor oil 60 that conforms to the standard of Japanese Pharmaceutical Excipients 2003. This test also used polyoxyethylene castor oil 10 and polyoxyethylene castor oil 35 that conform to the standard for polyoxyethylene castor oil in Japanese Pharmaceutical Excipients 2003 and in which the average number of moles of added ethylene oxide is 10 and 35, respectively.

First, each of the aqueous ophthalmic compositions (Example 4-1 and Comparative Examples 4-1 and 4-2) in an amount of 10 mL was placed in individual 10-mL eye drop containers made of PET and each container was equipped and sealed with a nozzle made of low-density polyethylene. Similarly, each of the aqueous ophthalmic compositions in an amount of 10 mL was placed in individual 10-mL glass ampoules (glass containers) and sealed. The aqueous ophthalmic compositions placed in the glass containers were used as controls since they were believed to have almost no adsorption of menthol and less menthol loss caused by volatilization or the like.

The samples were stored (in a manner such that the glass containers were placed in an upright position and the eye drop containers were placed in an inverted position) at 60° C. for three days, and then the concentration of menthol in each of the aqueous ophthalmic compositions was measured using gas chromatography. The amount of menthol loss relative to the control was calculated by subtracting the menthol concentration in the eye drop container from the menthol concentration in the glass container (control) for each aqueous ophthalmic composition having the same formulation. The rates of menthol loss in Example 4-1 and Comparative Example 4-2 relative to the amount of menthol loss in Comparative Example 4-1 were then calculated. The amount of menthol loss in Comparative Example 4-1 was defined as 100. The results are also shown in Table 12.

TABLE 12

| | Unit (w/v %) | | |
|---|---|---|---|
| | Example 4-1 | Comparative Example 4-1 | Comparative Example 4-2 |
| Polyoxyethylene castor oil 10 | 0.15 | — | — |
| Polyoxyethylene castor oil 35 | — | — | 0.15 |
| Polyoxyethylene hydrogenated castor oil 60 | 0.15 | 0.3 | 0.15 |
| l-menthol | 0.02 | 0.02 | 0.02 |
| Boric acid | 0.5 | 0.5 | 0.5 |
| Borax | 0.05 | 0.05 | 0.05 |
| Hydrochloric acid | q.s. | q.s. | q.s. |
| Sodium hydroxide | q.s. | q.s. | q.s. |
| Purified water | Balance | Balance | Balance |
| Total amount | 100 mL | 100 mL | 100 mL |
| pH | 7.3 | 7.3 | 7.3 |
| Rate of menthol loss relative to that of Comparative Example 4-1 defined as 100 | 73 | 100 | 85 |

When stored in the eye drop container, the aqueous ophthalmic composition (Example 4-1) containing both polyoxyethylene castor oil 10 and polyoxyethylene hydrogenated castor oil 60 as surfactants had significantly less menthol loss compared to the aqueous ophthalmic composition (Comparative Example 4-1) containing only polyoxyethylene hydrogenated castor oil 60 as a surfactant. When stored in the eye drop container, the aqueous ophthalmic composition (Comparative Example 4-2) containing polyoxyethylene castor oil 35 instead of polyoxyethylene castor oil 10 did not exhibit the effect of inhibiting reduction in the menthol concentration over time as high as Example 4-1, which contains polyoxyethylene castor oil 10.

Test Example 11

Preservative Efficacy Test (1)

Aqueous ophthalmic compositions shown in the following Table 13 (Example 5-1 and Comparative Examples 5-1 to 5-3) were prepared by a standard method, and a preservative efficacy test was performed for each of the aqueous ophthalmic compositions. Specifically, *Staphylococcus aureus* (ATCC6538) was inoculated on the surface of a soybean-casein digest slant medium and cultured at 33° C. for 24 hours. The cultured cells were aseptically collected using a platinum loop and suspended in an appropriate amount of sterile physiological saline to prepare a bacterial suspension containing viable cells at about $1\times10^5$ CFU/mL. The viable cell count in the suspension was measured by culturing separately. Subsequently, the aqueous ophthalmic compositions were filter-sterilized, and each of the aqueous ophthalmic compositions in an amount of 10 mL was placed in individual 15-mL CORNIA conical tubes (PET). The *Staphylococcus aureus* bacterial suspension (suspended in physiological saline) was inoculated into each of the aqueous ophthalmic compositions in such a manner that the viable cell count (final concentration) was about $10^3$ CFU/mL (3 log), and stirred thoroughly to prepare samples. The samples were stored at 23° C. for three days while shielded from light. After this 3-day period ended, each of the samples containing viable cells was adjusted to have an adequate concentration for counting, and the viable cell count was determined by a filtration method using a membrane filter. The viable cell count immediately after inoculation and the viable cell count after three days of storage in each sample were compared, and the reduction in viable cell count was calculated as log reduction. Bacterial culture for counting was performed at 33° C. for three days. This test used l-menthol that conforms to the standard of the Japanese Pharmacopoeia, 15th revision, and polyoxyethylene hydrogenated castor oil 60 that conforms to the standard of Japanese Pharmaceutical Excipients 2003. This test also used polyoxyethylene castor oil 10 and polyoxyethylene castor oil 35 that conform to the standard for polyoxyethylene castor oil in Japanese Pharmaceutical Excipients 2003 and in which the average number of moles of added ethylene oxide is 10 and 35, respectively. The results are also shown in Table 13.

TABLE 13

| | Unit (w/v %) | | | |
|---|---|---|---|---|
| | Example 5-1 | Comparative Example 5-1 | Comparative Example 5-2 | Comparative Example 5-3 |
| l-menthol | 0.02 | 0.02 | — | 0.02 |
| Polyoxyethylene castor oil 10 | 0.15 | — | 0.15 | — |
| Polyoxyethylene castor oil 35 | — | — | — | 0.15 |
| Polyoxyethylene hydrogenated castor oil 60 | 0.15 | 0.3 | 0.15 | 0.15 |
| Boric acid | 0.5 | 0.5 | 0.5 | 0.5 |
| Borax | 0.05 | 0.05 | 0.05 | 0.05 |
| Hydrochloric acid | q.s. | q.s. | q.s. | q.s. |
| Sodium hydroxide | q.s. | q.s. | q.s. | q.s. |
| Purified water | Balance | Balance | Balance | Balance |
| Total amount | 100 mL | 100 mL | 100 mL | 100 mL |
| pH | 7.3 | 7.3 | 7.3 | 7.3 |
| Log Reduction | 3.1 | 0.5 | 1.6 | 1.8 |

Little reduction in viable cell count was observed in Comparative Example 5-1, which contains only menthol. Reduction in viable cell count was 1.6 log in Comparative Example 5-2, which contains only polyoxyethylene castor oil 10. On the other hand, Example 5-1, which contains both menthol and polyoxyethylene castor oil 10, had preservative efficacy such that bacteria were killed. Such high preservative efficacy was not observed in Comparative Example 5-3, which contains polyoxyethylene castor oil 35 instead of polyoxyethylene castor oil 10.

Test Example 12

Preservative Efficacy Test (2)

Aqueous ophthalmic compositions shown in the following Table 14 (Examples 5-2 and 5-3 and Comparative Examples 5-4 and 5-5) were prepared by a standard method. Using these aqueous ophthalmic compositions, the viable cell count immediately after inoculation of *Staphylococcus aureus* and the viable cell count after seven days of storage in each sample were compared to calculate reduction in viable cell count as log reduction in the same manner as in Test Example 11. Bacterial culture for counting was performed at 33° C. This test used d-camphor that conforms to the standard of the Japanese Pharmacopoeia, 15th revision, and geraniol and polyoxyethylene hydrogenated castor oil 60 that conform to the standard of Japanese Pharmaceutical Excipients 2003. This test also used polyoxyethylene castor oil 10 and polyoxyethylene castor oil 35 that conform to the standard for polyoxyethylene castor oil in Japanese Pharmaceutical Excipients 2003 and in which the average number of moles of added ethylene oxide is 10 and 35, respectively. The results are also shown in Table 14.

TABLE 14

| | Unit (w/v %) | | | |
| --- | --- | --- | --- | --- |
| | Comparative Example 5-4 | Example 5-2 | Comparative Example 5-5 | Example 5-3 |
| Polyoxyethylene castor oil 10 | — | 0.025 | — | 0.4 |
| Polyoxyethylene castor oil 35 | — | — | 0.4 | — |
| Polyoxyethylene hydrogenated castor oil 60 | 0.175 | 0.15 | 0.5 | 0.5 |
| d-camphor | — | — | 0.05 | 0.05 |
| Geraniol | 0.003 | 0.003 | — | — |
| Boric acid | 0.5 | 0.5 | 0.5 | 0.5 |
| Borax | 0.05 | 0.05 | 0.05 | 0.05 |
| Sodium hydroxide | q.s. | q.s. | q.s. | q.s. |
| Hydrochloric acid | q.s. | q.s. | q.s. | q.s. |
| Purified water | q.s. | q.s. | q.s. | q.s. |
| pH | 7.3 | 7.3 | 7.3 | 7.3 |
| Log reduction | 3.7 | 4.7 | 1.9 | 2.5 |

As is clear from Table 14, Example 5-2, which contains polyoxyethylene castor oil 10 and geraniol, had significant reduction in the viable cell count compared to Comparative Example 5-4, which contains only geraniol, indicating high preservative efficacy. Further, Example 5-3, which contains polyoxyethylene castor oil 10 and d-camphor, had significant reduction in the viable cell count compared to Comparative Example 5-5, which contains polyoxyethylene castor oil 35 and d-camphor, indicating high preservative efficacy.

From the above results, it was confirmed that high preservative efficacy against *Staphylococcus aureus* is exhibited when a terpenoid is contained together with polyoxyethylene castor oil in which the average number of moles of added ethylene oxide is 2 to 12.

Test Example 13

Preservative Efficacy Test (3)

Aqueous ophthalmic compositions shown in the following Table 15 (Example 5-4 and Comparative Example 5-6) were prepared by a standard method. Using these aqueous ophthalmic compositions, the viable cell count immediately after inoculation of *Staphylococcus aureus* and the viable cell count immediately after inoculation of *E. coli* were compared with the viable cell count after storage in each sample to calculate reduction in viable cell count as log reduction in the same manner as in Test Example 11. Bacterial culture for counting was performed at 33° C. for three days for *Staphylococcus aureus* and for seven days for *E. coli*. This test used eucalyptus oil that conforms to the standard of the Japanese Pharmacopoeia, 15th revision, and polyoxyethylene hydrogenated castor oil 60 that conforms to the standard of Japanese Pharmaceutical Excipients 2003. This test also used polyoxyethylene castor oil 10 that conforms to the standard for polyoxyethylene castor oil in Japanese Pharmaceutical Excipients 2003 and in which the average number of moles of added ethylene oxide is 10. The results are also shown in the following Table 15.

TABLE 15

| | Unit (w/v %) | |
| --- | --- | --- |
| | Comparative Example 5-6 | Example 5-4 |
| Polyoxyethylene castor oil 10 | — | 0.025 |
| Polyoxyethylene hydrogenated castor oil 60 | 00.175 | 0.15 |
| *Eucalyptus* oil | 0.003 | 0.003 |
| Boric acid | 0.5 | 0.5 |
| Borax | 0.05 | 0.05 |
| Sodium hydroxide | q.s. | q.s. |
| Hydrochloric acid | q.s. | q.s. |
| Purified water | q.s. | q.s. |
| pH | 7.3 | 7.3 |
| Log reduction *Staphylococcus aureus* (3 days) | 2.5 | 3.3 |
| *E. coli* (7 days) | 0 | 0.3 |

As is clear from Table 15, Example 5-4, which contains polyoxyethylene castor oil 10 and eucalyptus oil, had significant reduction in the number of *Staphylococcus aureus* compared to Comparative Example 5-6, which contains only eucalyptus oil, indicating high preservative efficacy. In Example 5-4, which contains polyoxyethylene castor oil 10 and eucalyptus oil, reduction in the number of *E. coli* was observed, whereas no effect on the number of *E. coli* was observed in Comparative Example 5-6, which contains only eucalyptus oil.

The above results reveal that high preservative efficacy is exhibited against not only *Staphylococcus aureus* but also *E. coli* when a terpenoid is contained together with polyoxyethylene castor oil in which the average number of moles of added ethylene oxide is 2 to 12.

Test Example 14

Sensory Test

Aqueous ophthalmic compositions having the formulations shown in Table 16 (Example 6-1 and Comparative Example 6-1) were prepared and evaluated for cooling sensation according to a visual analogue scale (VAS). Specifically, drops of each aqueous ophthalmic composition were applied to the eyes of six panelists, and on subjective symptom assessment sheets, the panelists wrote down the degree of cooling sensation that they felt immediately after application and 5 minutes after application. The intensity of subjective symptoms was subsequently measured in length (cm) based on the subjective symptom assessment sheets, and the length (cm) was used as cooling sensation score: the length was 0 cm if no cooling was sensed, 5 cm if cooling was sensed, and 10 cm if cooling was strongly sensed. The cooling sensation was evaluated by calculating the average score value of the six panelists immediately after application and the average score value of the six panelists 5 minutes after application. The results are shown in Table 16.

TABLE 16

| | | Example 6-1 | Comparative Example 6-1 |
|---|---|---|---|
| | Unit (w/v %) | | |
| Polyoxyethylene castor oil 10 | | 0.05 | — |
| l-menthol | | 0.01 | 0.01 |
| Polysorbate 80 | | 0.45 | 0.5 |
| Sodium chloride | | 0.4 | 0.4 |
| Potassium chloride | | 0.1 | 0.1 |
| Boric acid | | 1 | 1 |
| Borax | | 0.1 | 0.1 |
| Purified water (mL) | | Balance | Balance |
| pH | | 7.15 | 7.15 |
| Cooling sensation score | Immediately after application to the eyes | 7.5 | 6.9 |
| | 5 minutes after application to the eyes | 5.4 | 3.0 |

As shown in Table 16, the cooling sensation scores of both the compositions were similar immediately after application; however, in the aqueous ophthalmic composition containing polyoxyethylene castor oil 10, cooling sensation was still clearly observed 5 minutes after application.

The above results reveal that the aqueous ophthalmic composition of the present invention, which contains both polyoxyethylene castor oil 10 and a terpenoid, has the effect of maintaining the cooling sensation of a terpenoid.

Preparation Examples

According to the formulations shown in Tables 17 and 18, eye drops (Preparation Examples 1 to 7), eye wash (Preparation Example 8), solution for wearing a contact lens (Preparation Example 9), and multi-purpose contact lens solution (Preparation Example 10) are prepared by standard methods. The unit of osmotic pressure is mOsm (milliosmole).

TABLE 17

| | Preparation Example | | | | |
|---|---|---|---|---|---|
| Unit: g/100 mL | 1 | 2 | 3 | 4 | 5 |
| Polyoxyethylene castor oil 35 | 0.050 | — | 0.400 | — | — |
| Polyoxyethylene castor oil 10 | 0.100 | 0.050 | 0.100 | 0.500 | 0.350 |
| Polyoxyethylene castor oil 3 | — | — | 0.500 | 0.085 | — |
| l-menthol | 0.010 | — | 0.040 | 0.015 | 0.020 |
| d-camphor | 0.005 | — | 0.010 | — | — |
| d-borneol | 0.003 | — | — | 0.015 | 0.001 |
| Geraniol | — | 0.005 | 0.003 | — | 0.001 |
| Neostigmine methylsulfate | — | 0.010 | — | — | — |
| Tetrahydrozoline hydrochloride | 0.010 | — | — | — | — |
| Chlorpheniramine maleate | 0.030 | 0.015 | 0.010 | — | 0.030 |
| Sodium azulene sulfonate | — | — | — | — | 0.020 |
| Berberine sulfate | — | — | — | — | 0.005 |
| Dipotassium glycyrrhizate | 0.250 | — | — | — | — |
| Pyridoxine hydrochloride | 0.100 | 0.100 | 0.050 | — | — |
| Aminoethylsulfonic acid | — | — | 0.500 | — | — |
| Sodium chondroitin sulfate | 0.100 | 0.500 | 0.500 | — | 0.500 |
| Sodium edetate | 0.010 | 0.010 | — | — | 0.050 |
| Sodium chloride | — | — | — | 0.450 | — |
| Potassium chloride | — | — | — | 0.080 | — |
| Boric acid | 1.500 | 1.800 | 1.000 | — | 1.500 |
| Borax | 0.500 | 0.350 | 0.050 | — | 0.300 |
| Hydroxyethyl cellulose | — | — | — | 0.250 | — |
| Hydroxypropyl methylcellulose | — | — | — | 0.250 | — |
| Glycerin | — | — | — | 0.100 | — |
| Poloxamer 407 | — | 0.100 | — | — | — |
| Polysorbate 80 | 0.500 | — | 0.300 | 0.500 | 0.200 |
| Polyoxyethylene hydrogenated castor oil 60 | — | 0.200 | — | — | 0.500 |
| Potassium sorbate | — | 0.050 | — | — | — |
| Dibutylhydroxytoluene | — | — | — | — | 0.001 |
| Chlorobutanol | — | — | 0.150 | — | — |
| Hydrochloric acid | q.s. | q.s. | q.s. | q.s. | q.s. |
| Sodium hydroxide | q.s. | q.s. | q.s. | q.s. | q.s. |
| Purified water | q.s. | q.s. | q.s. | q.s. | q.s. |
| Total amount | 100 mL | 100 mL | 100 mL | 100 mL | 100 mL |
| pH | 7.00 | 7.0 | 5.8 | 7.5 | 7.0 |
| Osmotic pressure | 370 | 300 | 300 | 360 | 350 |

TABLE 18

Unit: g/100 mL

| | Preparation Example | | | | |
|---|---|---|---|---|---|
| | 6 | 7 | 8 | 9 | 10 |
| Polyoxyethylene castor oil 35 | 0.500 | 0.200 | — | — | — |
| Polyoxyethylene castor oil 10 | 0.010 | 0.020 | 0.100 | 0.050 | 0.100 |
| Polyoxyethylene castor oil 3 | — | — | — | — | 0.100 |
| l-menthol | 0.030 | 0.050 | 0.002 | 0.025 | 0.010 |
| d-camphor | — | — | — | — | — |
| d-borneol | — | — | 0.001 | — | — |
| Geraniol | — | 0.002 | — | — | — |
| Dipotassium glycyrrhizate | — | — | — | 0.025 | — |
| Pyridoxine hydrochloride | — | — | — | 0.010 | — |
| Tocopherol acetate | — | — | — | 0.005 | — |
| Aminoethylsulfonic acid | — | — | — | 0.020 | — |
| Sodium chondroitin sulfate | — | 0.500 | — | 0.040 | — |
| Sodium edetate | — | 0.004 | — | 0.050 | — |
| Sodium chloride | 0.400 | 0.300 | 0.450 | — | 0.700 |
| Potassium chloride | 0.080 | 0.100 | 0.100 | — | 0.050 |
| Disodium hydrogen phosphate | — | — | 0.150 | — | 0.150 |
| Sodium dihydrogen phosphate | — | — | 0.050 | — | 0.200 |
| Boric acid | 1.000 | 1.100 | — | 1.200 | — |
| Borax | 0.200 | 0.300 | — | 0.300 | — |
| Hydroxyethyl cellulose | 0.050 | — | — | — | — |
| Hydroxypropyl methylcellulose | — | — | 0.100 | 0.300 | — |
| Poloxamer 407 | 0.050 | — | — | — | — |
| Polysorbate 80 | — | — | 0.300 | 0.500 | — |
| Polyoxyethylene hydrogenated castor oil 60 | 0.300 | 0.300 | — | — | 0.300 |
| Potassium sorbate | 0.050 | 0.080 | — | — | — |
| Polyhexamethylene biguanide | — | — | — | — | 0.0001 |
| Ethanol | 0.100 | — | — | — | — |
| Hydrochloric acid | q.s. | q.s. | q.s. | q.s. | q.s. |
| Sodium hydroxide | q.s. | q.s. | q.s. | q.s. | q.s. |
| Purified water | q.s. | q.s. | q.s. | q.s. | q.s. |
| Total amount | 100 mL | 100 mL | 100 mL | 100 mL | 100 mL |
| pH | 7.4 | 7.5 | 6.2 | 7.0 | 7.5 |
| Osmotic pressure | 350 | 360 | 300 | 350 | 290 |

The invention claimed is:

1. An aqueous ophthalmic composition comprising (A) polyoxyethylene castor oil in which the average number of moles of added ethylene oxide is 2 to 12, and (B) terpenoid.

2. The aqueous ophthalmic composition according to claim 1, wherein component (A) is at least one member selected from the group consisting of polyoxyethylene castor oil 3 and polyoxyethylene castor oil 10.

3. The aqueous ophthalmic composition according to claim 1, wherein component (B) is contained in a total amount of 0.01 to 1,000 parts by weight per 100 parts by weight of the total amount of component (A).

4. The aqueous ophthalmic composition according to claim 1, which further comprises a nonionic surfactant other than component (A).

5. The aqueous ophthalmic composition according to claim 3, which further comprises a nonionic surfactant other than component (A).

6. The aqueous ophthalmic composition according to claim 2, wherein component (B) is contained in a total amount of 0.01 to 1,000 parts by weight per 100 parts by weight of the total amount of component (A).

7. The aqueous ophthalmic composition according to claim 2, which further comprises a nonionic surfactant other than component (A).

8. The aqueous ophthalmic composition according to claim 6, which further comprises a nonionic surfactant other than component (A).

* * * * *